US010413278B2

(12) United States Patent
Chen et al.

(10) Patent No.: US 10,413,278 B2
(45) Date of Patent: Sep. 17, 2019

(54) METHODS AND DEVICES FOR ULTRASOUND CONTRAST-ASSISTED THERAPY

(71) Applicant: University of Pittsburgh—Of the Commonwealth System of Higher Education, Pittsburgh, PA (US)

(72) Inventors: Xucai Chen, Pittsburgh, PA (US); Jianjun Wang, Pittsburgh, PA (US); John J. Pacella, Pittsburgh, PA (US); Flordeliza S. Villanueva, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 298 days.

(21) Appl. No.: 14/409,409

(22) PCT Filed: Jun. 27, 2013

(86) PCT No.: PCT/US2013/048326
§ 371 (c)(1),
(2) Date: Dec. 18, 2014

(87) PCT Pub. No.: WO2014/004912
PCT Pub. Date: Jan. 3, 2014

(65) Prior Publication Data
US 2015/0141817 A1 May 21, 2015

Related U.S. Application Data

(60) Provisional application No. 61/665,781, filed on Jun. 28, 2012.

(51) Int. Cl.
*A61B 8/08* (2006.01)
*A61N 7/00* (2006.01)
(Continued)

(52) U.S. Cl.
CPC .......... *A61B 8/481* (2013.01); *A61K 41/0028* (2013.01); *A61K 49/223* (2013.01);
(Continued)

(58) Field of Classification Search
CPC .. A61K 41/00; A61K 49/223; A61K 41/0028; A61M 31/00; A61M 37/00;
(Continued)

(56) References Cited

U.S. PATENT DOCUMENTS 5,558,092 A * 9/1996 Unger .................. A61B 8/0833
600/439
5,695,460 A * 12/1997 Siegel .............. A61B 17/22004
600/458

(Continued)

FOREIGN PATENT DOCUMENTS

WO WO 1999/042138 8/1999
WO WO 2008/017997 2/2008

OTHER PUBLICATIONS

Wilkens, Volker, and Hans-Peter Reimann. "Output intensity measurement on a diagnostic ultrasound machine using a calibrated thermoacoustic sensor." Journal of Physics: Conference Series. vol. 1. No. 1. IOP Publishing, 2004. (Year: 2004).*

(Continued)

*Primary Examiner* — Luther Behringer
*Assistant Examiner* — Sean D Mattson
(74) *Attorney, Agent, or Firm* — Klarquist Sparkman, LLP

(57) ABSTRACT

Various methods of performing ultrasound contrast assisted therapy are provided. One such method includes delivering a plurality of microbubble-based ultrasound contrast agents to a target area and disrupting the microbubble-based ultrasound contrast agents by delivering tone bursts of ultrasound to the target area. The oscillation of the microbubble-based ultrasound contrast agents can be achieved by delivering ultrasound tone bursts of greater than 5 acoustic cycles with a pulse repetition frequency of between 0.01 and 20 Hz, with pressure greater than 0.3 MPa.

16 Claims, 26 Drawing Sheets

Sonothrombolysis: Long-tone burst?

In vitro setup: 1 MHz, 1.5 MPa, PRF 1/3 Hz, tone burst duration variable

Lytic effect indicates a plateau in the effect of number of acoustic cycle

(51) Int. Cl.
   A61K 41/00      (2006.01)
   A61K 49/22      (2006.01)
   A61M 37/00      (2006.01)
   A61N 7/02       (2006.01)
   A61M 5/00       (2006.01)
   A61M 31/00      (2006.01)
   A61B 17/00      (2006.01)
   A61B 90/00      (2016.01)

(52) U.S. Cl.
   CPC ........ *A61M 5/007* (2013.01); *A61M 37/0092* (2013.01); *A61N 7/00* (2013.01); *A61N 7/02* (2013.01); *A61B 8/5261* (2013.01); *A61B 2017/00181* (2013.01); *A61B 2017/00194* (2013.01); *A61B 2090/373* (2016.02); *A61B 2090/378* (2016.02); *A61M 31/005* (2013.01); *A61N 2007/0039* (2013.01); *A61N 2007/0052* (2013.01)

(58) Field of Classification Search
   CPC .... A61M 5/00; A61M 5/007; A61M 37/0092; A61M 31/005; A61N 2007/00; A61N 7/00; A61N 7/02; A61N 2007/0052; A61N 2007/0039; A61B 2017/00; A61B 2090/00; A61B 8/00; A61B 8/481; A61B 8/5291; A61B 2090/378; A61B 2090/373; A61B 2017/00194; A61B 2017/00181
   See application file for complete search history.

(56)            References Cited

U.S. PATENT DOCUMENTS

| | | | | |
|---|---|---|---|---|
| 6,017,310 | A * | 1/2000 | Johnson ............... | A61K 49/223 600/458 |
| 2005/0084538 | A1* | 4/2005 | Dayton ................ | A61B 8/4483 424/489 |
| 2006/0264809 | A1* | 11/2006 | Hansmann ............ | A61B 17/22 604/22 |
| 2008/0319375 | A1* | 12/2008 | Hardy .................. | A61K 9/0009 604/22 |
| 2010/0143241 | A1 | 6/2010 | Johnson et al. | |
| 2011/0201974 | A1* | 8/2011 | Soltani ................ | A61K 9/0009 601/2 |

OTHER PUBLICATIONS

Şen, Taner, Omaç Tüfekçioğlu, and Yavuzer Koza. "Mechanical index." Anatolian journal of cardiology 15.4 (2015): 334. (Year: 2015).*

Leeman, Jonathan E., et al. "Effect of acoustic conditions on microbubble-mediated microvascular sonothrombolysis." Ultrasound in medicine & biology 38.9 (2012): 1589-1598. (Year: 2012).*

Bekeredjian, et al. "Use of Ultrasound Contrast Agents for Gene or Drug Delivery in Cardiovascular Medicine," *Journal of the American College of Cardiology* 45 (2005): 329-335.

Choi, et al., "Noninvasive and localized blood-brain barrier disruption using focused ultrasound can be achieved at short pulse lengths and low pulse repetition frequencies," *Journal of Cerebral Blood Flow & Metabolism* 31 (2011): 725-737.

Datta, et al. "Correlation of cavitation with ultrasound enhancement of thrombolysis," *Ultrasound in medicine & biology* 32 (2006): 1257-1267.

Datta, et al. "Ultrasound-Enhanced Thrombolysis Using Definity$^{®}$ as a Cavitation Nucleation Agent." *Ultrasound in medicine & biology* 34 (2008): 1421-1433.

Forbes, et al., "Examination of Inertial Cavitation of Optison™ in Producing Sonoporation of Chinese Hamster Ovary Cells." *Ultrasound in Medicine and Biology* 34 (2008): 2009-2018.

Goertz, et al. "Contrast Agent Kinetics in the Rabbit Brain During Exposure to Therapeutic Ultrasound," *Ultrasound in Medicine and Biology* 36 (2010): 916-924.

Kutty, et al. "Sonothrombolysis of intra-catheter aged venous thrombi using microbubble enhancement and guided three-dimensional ultrasound pulses." *Journal of the American Society of Echocardiography* 23 (2010): 1001-1006.

Nedelmann, et al, "Combined contrast-enhanced ultrasound and rt-PA treatment is safe and improves impaired microcirculation after reperfusion of middle cerebral artery occlusion." *Journal of Cerebral Blood Flow & Metabolism* 30 (2010): 1712-1720.

O'Reilly, et al. "Focused-Ultrasound Disruption of the Blood-Brain Barrier Using Closely-Timed Short Pulses: Influence of Sonication Parameters and Injection Rate", *Ultrasound in Medicine and Biology* 37 (2011): 587-594.

Prokop, et al. "Cavitational mechanisms in ultrasound-accelerated fibrinolysis," *Ultrasound in medicine & biology* 33 (2007): 924-933. (Abstract only).

Sorace, et al., "Microbubble-mediated ultrasonic techniques for improved chemotherapeutic delivery in cancer," *Journal Drug Target* 20 (2012): 43-54.

Teupe, et al. "Vascular Gene Transfer of Phosphomimetic Endothelial Nitric Oxide Synthase (S1177D) Using Ultrasound-Enhanced Destruction of Plasmid-Loaded Microbubbles Improves Vasoreactivity," *Circulation* 105 (2002): 1104-1109.

Tiukinhoy-Laing, et al. "Ultrasound-facilitated thrombolysis using tissue-plasminogen activator-loaded echogenic liposomes," *Thrombosis Research* 119 (2007): 777-784.

Tung, et al. "The mechanism of interaction between focused ultrasound and microbubbles in blood-brain barrier opening in mice," *Journal of the Acoustic Society of America* 130 (2011): 3059-3067.

Xie, et al. "Diagnostic ultrasound combined with glycoprotein IIb/IIIa-targeted microbubbles improves microvascular recovery after acute coronary thrombotic occlusions." *Circulation* 119 (2009): 1378-1385.

* cited by examiner

Brightfield imaging at 25 Mfps:
Resonance phenomena, cavitation 2.25 MHz. left 0.5 MPa, right 1.0 MPa.

Result: Brightfield example-Lipid MB

Selected brightfield frames of US-induced MB vibration and breaking (from 25 Mfps movie).

Brightfield example: Thrombus Lysis

Selected brightfield frames of US-induced lipid MB vibration and invagination of thrombus (1 MHz, 1.5 MPa, 5Mfps).

FIG. 6
Fluorescence imaging of polymer MB shell
Brightfield at *25 Mfps*
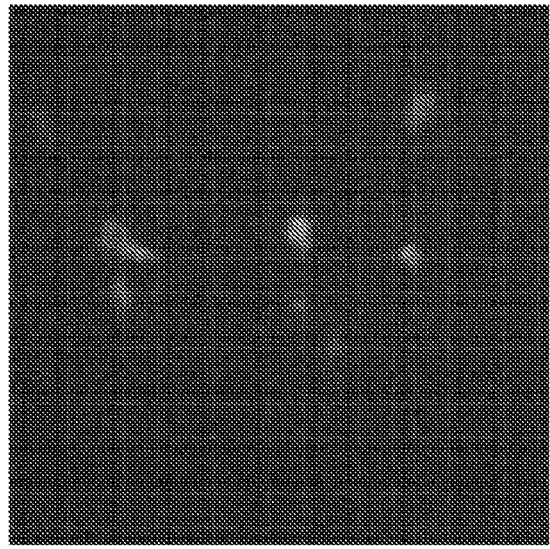
Brightfield reveals large amplitude oscillation
1 MHz, 2 MPa
Fluorescence at *25 Mfps*
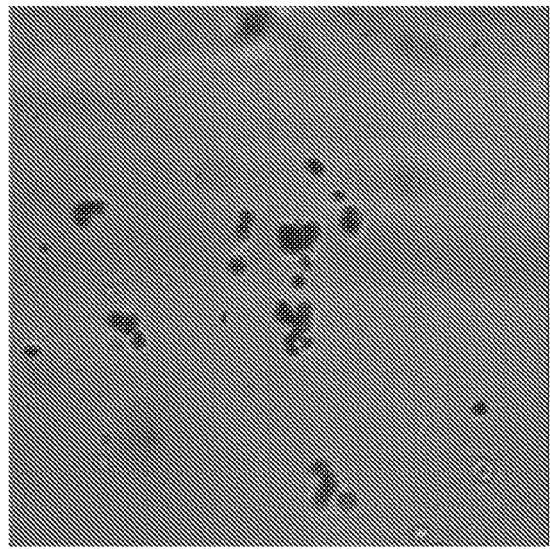
Fluorescence reveals that the shell oscillates at smaller amplitude, indicating gas escape from the shell

Stem cell membrane displaced by lipid MB

Stem cell

1 MHz, 1 MPa, 16 Mfps

FL: 250 kfps
Lipid MB + Beads
US 1.5 MPa

Bits 2-9 and 5-12

Beads are throwing off
Large movement
Jetting?

FL: 500 kfps
Lipid MB + Beads
US 1.0 MPa

Bits 2-9 and 5-12

Beads are throwing off
More so in front
Jetting?

FL: 500 kfps
Lipid MB + Beads
US 0.5 MPa

Bits 2-9 and 5-12

Beads are throwing off
More so in front
Jetting?

METHODS AND DEVICES FOR ULTRASOUND CONTRAST-ASSISTED THERAPY

CROSS REFERENCE TO RELATED APPLICATIONS

This is the U.S. National Stage of International Application No. PCT/US2013/048326, filed Jun. 27, 2013, which was published in English under PCT Article 21(2), which in turn claims the benefit of U.S. Provisional Application No. 61/665,781, which was filed on Jun. 28, 2012. The provisional application is incorporated herein by reference in its entirety.

FIELD

This disclosure is related to ultrasound (US) contrast agents and, in particular, to the use of such contrast agents in combination with ultrasound devices for therapeutic purposes.

BACKGROUND

Ultrasound contrast agents have been used to improve ultrasonic imaging. In addition, ultrasound contrast agents, such as encapsulated gas microbubbles (MB), can be used for therapeutic applications in which the ultrasound beam disrupts the microbubble and/or cell membranes to delivery some therapeutic agent (e.g., a drug). However, conventional techniques of using ultrasound for therapeutic purposes have significant limitations and, as such, improvements to methods and systems for performing ultrasound contrast assisted therapy are much needed.

SUMMARY

As disclosed in more detail herein, various methods of performing ultrasound contrast assisted therapy are provided. One such method includes delivering a plurality of microbubble-based ultrasound contrast agents to a target area and disrupting the microbubble-based ultrasound contrast agents by delivering tone bursts of ultrasound to the target area. The disrupting of the microbubble-based ultrasound contrast agents can be achieved by delivering ultrasound tone bursts of greater than 5 acoustic cycles with a pulse repetition frequency of between 0.01 and 20 Hz and pressure amplitude of greater than 0.3 MPa. In some embodiments, the pressure amplitude can be lower, such as 0.2 MPa or greater, or alternatively, 0.25 MPa or greater.

In some embodiments, the method of claim 1, wherein at least some of the microbubble-based ultrasound contrast agents comprises a treatment agent, such as one or more drugs or genes. In some embodiments, the treatment agent comprises a protein and/or thrombolytic agent such as tissue plasminogen activator.

In some embodiments, the ultrasound tone bursts are between 1,000 and 2,000 acoustic cycles, the pulse repetition frequency is between 0.2 and 1 Hz, the ultrasound frequency is between about 0.25 MHz and 10 MHz, and/or an amplitude of ultrasound pulses forming the ultrasound tone bursts is between about 0.3 and 1.9 MPa. In some embodiments, a time-averaged ultrasound intensity can be less than 0.5 W/cm². In some embodiments, a time-averaged ultrasound intensity can be less than 0.1 W/cm². This can be achieved because a relatively low pulse repetition frequency is effective when relatively long tone bursts are used.

In yet additional embodiments, the method can include visualizing acoustic behaviors of the microbubble-based ultrasound contrast agents using high speed imaging under brightfield and fluorescence conditions, such as by using the novel high speed imaging systems described herein.

In yet another embodiment, a method can include determining an optimal tone burst length for a plurality of microbubble-based ultrasound contrast agents. Once the optimal tone burst length is determined, the method can further include delivering the plurality of microbubble-based ultrasound contrast agents to a target area of a subject and disrupting the microbubble-based ultrasound contrast agents by delivering tone bursts of ultrasound to the target area at the determined optimal tone burst length. In some embodiments, the disrupting of the microbubble-based ultrasound contrast agents can comprise delivering ultrasound tone bursts of greater than 5 acoustic cycles with at least one of a (1) pulse repetition frequency of between 0.01 and 20 Hz or (2) a pressure amplitude of greater than 0.3 MPa. In other embodiments, the act of determining the optimal tone burst length can comprise selecting the optimal tone burst length based on an acoustic pressure, bubble type, a bubble concentration, or any combination of the three.

The foregoing and other objects, features, and advantages of the invention will become more apparent from the following detailed description, which proceeds with reference to the accompanying figures.

BRIEF DESCRIPTION OF THE DRAWINGS

FIG. 6 illustrates a comparison between brightfield and fluorescence movies of MB oscillation.

DETAILED DESCRIPTION

Figure 1:
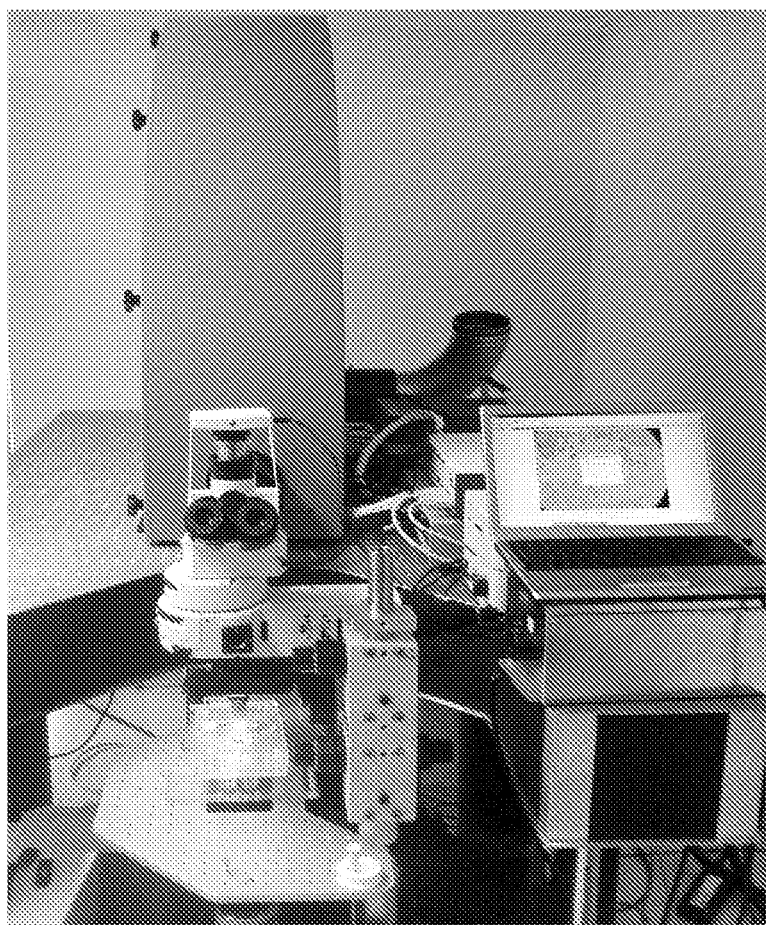
FIG. 1 illustrates a rotating mirror camera system used for the study of microbubble dynamics and the potential therapeutic effects under ultrasound.

Novel methods and devices for ultrasound contrast assisted therapy are disclosed herein. Such methods and devices can be used, for example, in connection with the treatment of thrombotic conditions and tumors.

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

As used herein, the term "treatment agent" refers to any agent that can be administered to a living organism for an effect in the treated organism, such as a drug, gene, ligand, or other agent that can be delivered by a microbubble and which can have an effect on the living organisms (e.g., a patient or subject). As used herein, the term "anti-thrombus agent" refers to any agent that can be used to reduce thrombus formation, such as thrombolytic drugs like streptokinase or tissue plasminogen activator (tPA).

As described herein, ultrasound assisted therapies, such as ultrasound-induced microbubble destruction can enhance thrombolysis and drug or gene delivery for cardiovascular disease and other treatments. Visualization of US-MB-cell interactions, which occur in a nano-second time scale due to the physics of ultrasound yield insights into therapeutically relevant microbubble dynamics, which can help improve the design and selection of new US-MB-mediated therapies.

High speed fluorescence imaging has unique advantages: we can visualize MB acoustic behaviors in vivo; we can derive information on responses of MB shells in addition to gas behavior in an ultrasound field; and we can visualize fate of fluorescent therapeutics loaded on the MB. The novel system described herein includes an integrated microscopy-high frame rate imaging system that allows for visualization of microbubble acoustic behaviors under brightfield and fluorescence conditions in order to ultimately perform high speed MB imaging in vivo.

FIG. 1 illustrates a rotating mirror camera system used for the study of microbubble dynamics and the potential therapeutic effects under ultrasound. A custom optical table is used to support the camera system to reduce the effect of room vibration. The microscope is mounted on an extension table with a translation stage. The customized microscope can have a dual focusing block arrangement to allow focusing on the sample while keeping the optical alignment with the camera system. The illuminator can have a side port to accept the laser light source for florescence imaging. The microscope image is diverted to the rotating mirror system. The imaging system is capable of 25 Mfps for both brightfield and fluorescence imaging for 128 frames, with a frame size of 920×616 pixels. As described herein, ultrasound (US)-assisted therapies such as US-induced microbubble (MB) destruction have potential to enhance thrombolysis and drug or gene therapy. Cavitation caused lysis, shear stress, microjetting, microstreaming, etc., are the likely mechanism for this beneficial effect. The high speed imaging system described herein can be used to visualize microbubble behaviors. High speed fluorescence imaging allows unique in vitro and in vivo microscopic observations of MB acoustic behavior and fluid dynamics in its surrounding. MIP processing of high speed movie allows a PIV type of analysis.

Figure 2:
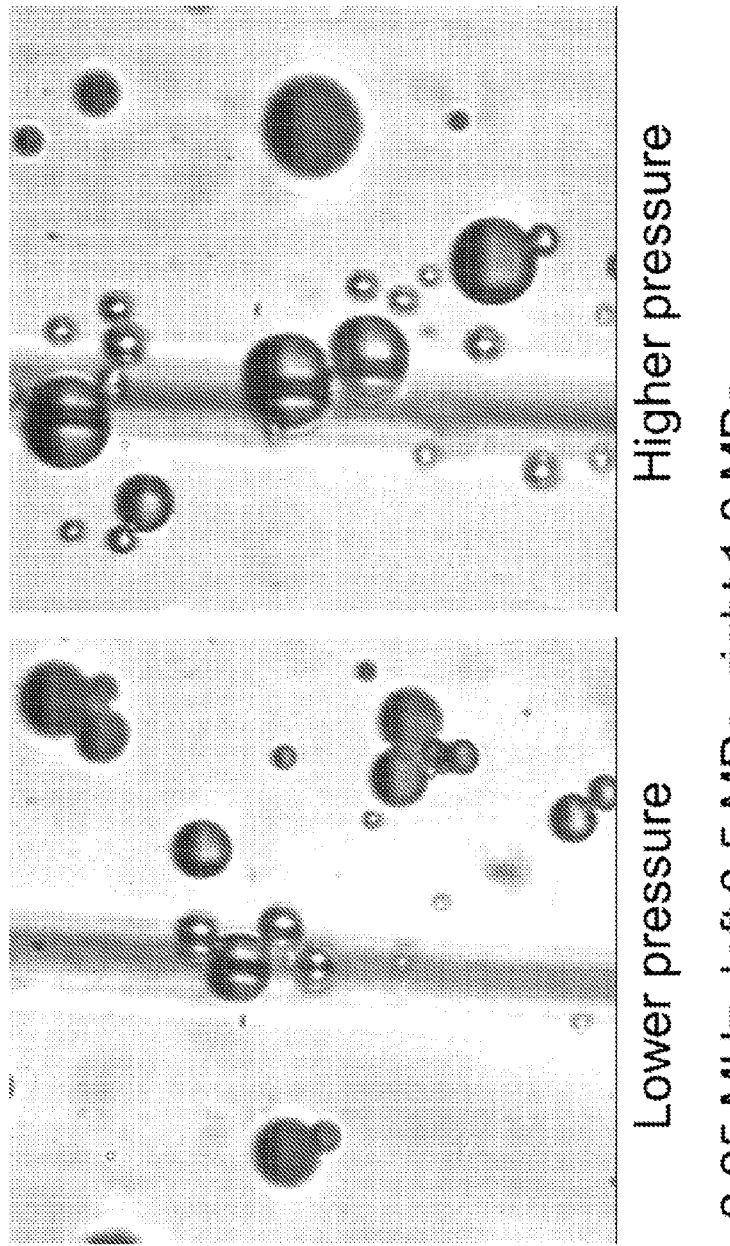
FIG. 2 illustrates a brightfield example of MB oscillation taken at 25 Million frames per second (Mfps).

FIG. 2 illustrates a brightfield example. Those movies are taken at 25 Mfps in brightfield mode, showing Lipid MB under ultrasound. Under low pressure excitation, microbubble expansion and contraction, and other resonance phenomena are observed. When higher acoustic pressure is used, microbubbles go through large amplitude oscillation, shape deformation, and eventually break.

Figure 3:
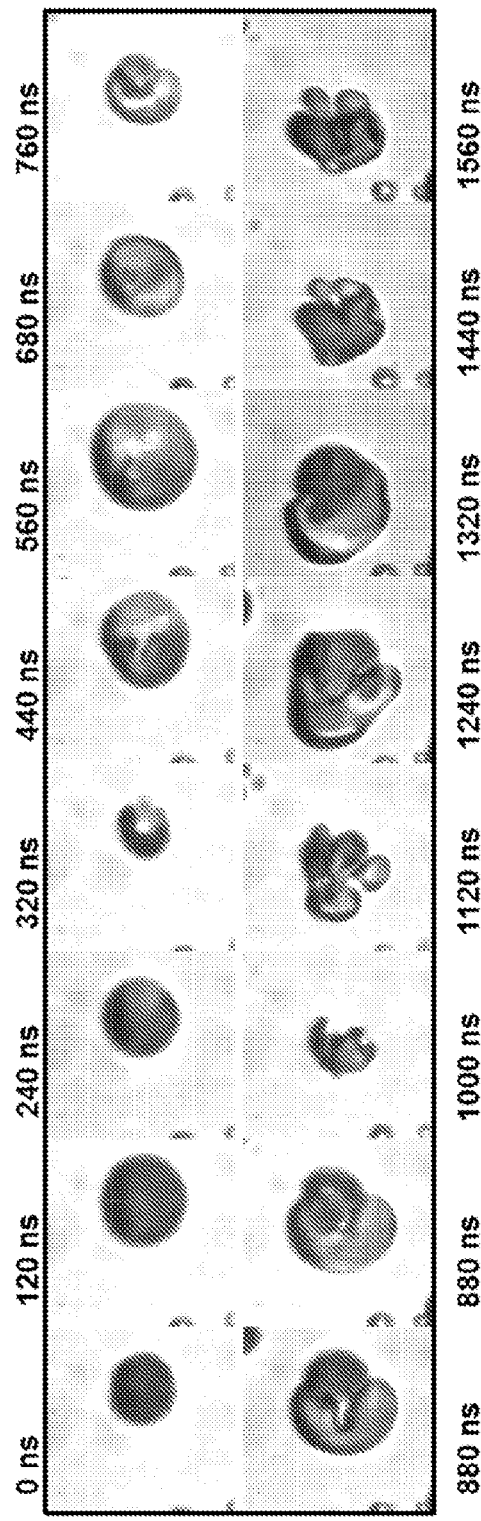
FIG. 3 illustrates selected brightfield frames from a 25 Mfps movie of US-induced MB vibration, jet formation, and breaking.

FIG. 3 illustrates selected brightfield frames from a 25 Mfps movie of US-induced MB vibration, jet formation, and breaking.

Figure 4:
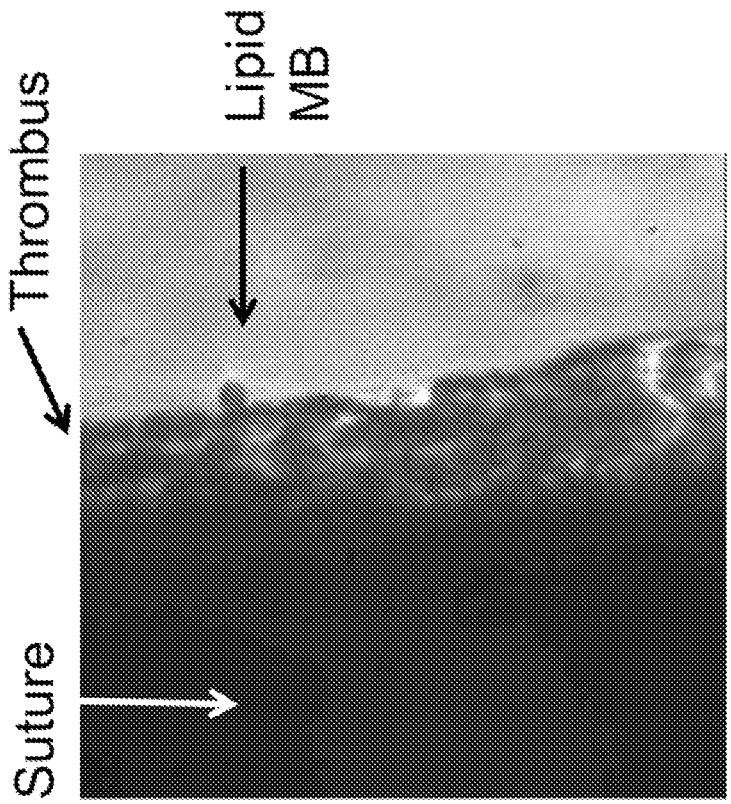
FIG. 4 illustrates a brightfield example of thrombus lysis—ultrasound induced MB vibration near a thrombus.

FIG. 4 illustrates a brightfield example of thrombus lysis—US-induced MB vibration near a thrombus. Large amplitude oscillation against the clot surface is seen, with possible invagination of the thrombus.

Figure 5:
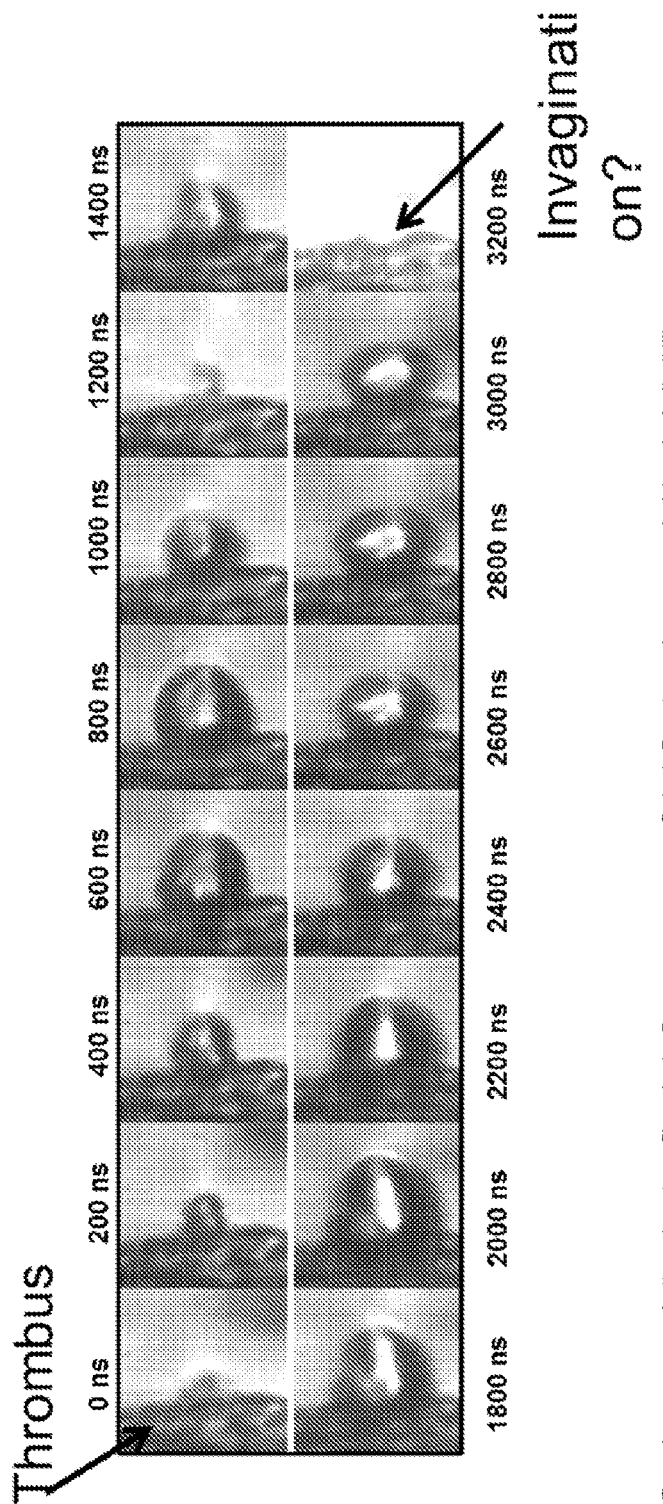
FIG. 5 illustrates a brightfield example of thrombus lysis-selected frames of ultrasound induced MB vibration near a thrombus.

FIG. 5 is still images from the brightfield movie showing the interactions in vitro between a lipid microbubble and a thrombus when subjected to ultrasound. Note the high amplitude oscillations of the microbubble against the thrombus. Interestingly, the microbubble disappears during imaging, and an invagination appears to be left behind in the thrombus.

FIG. 6 illustrates a comparison between brightfield and fluorescence, with both brightfield and fluorescence movies at 25 Mfps. Fluorescence imaging can help determine the fate of the microbubble shell. The bright field movie shows violent oscillations and the fluorescence movie is under identical ultrasound conditions. The movie shows that the shell of the bubble oscillates at much smaller amplitude. This suggests that the violent oscillations seen on the brightfield movie must be from the gas that has escaped from the shell. This observation may have implications for US mediated therapy such as drug and gene delivery.

Figure 7:
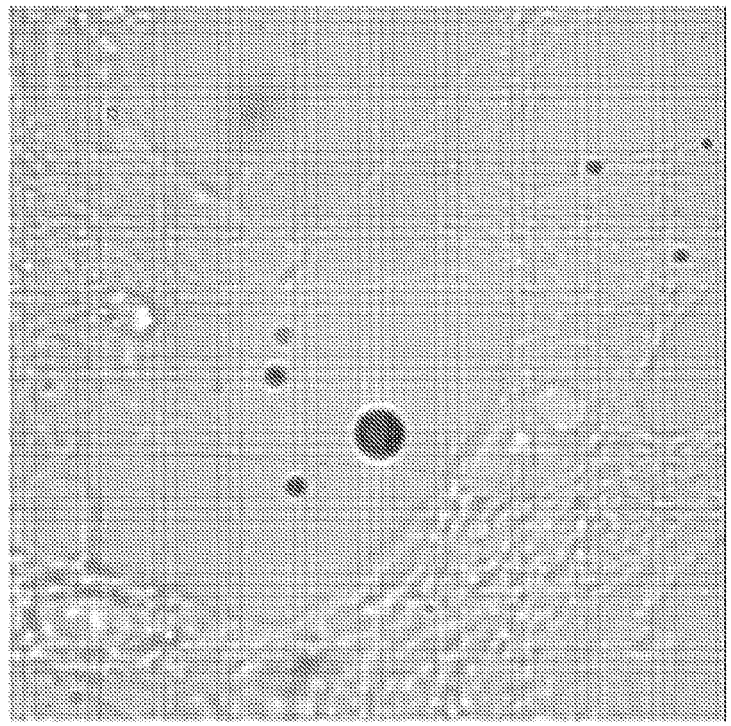
FIG. 7 illustrates an image of a lipid MB interacting with stem cells under ultrasound.

FIG. 7 illustrates another image of a lipid MB. In this figure, a stem cell is shown with a lipid MB next to it. Under ultrasound, large amplitude oscillations of the MB are observed. The cell membrane can be displaced by the microbubble, which has been shown to facilitate transmembrane transport of macromolecules.

Figure 8:
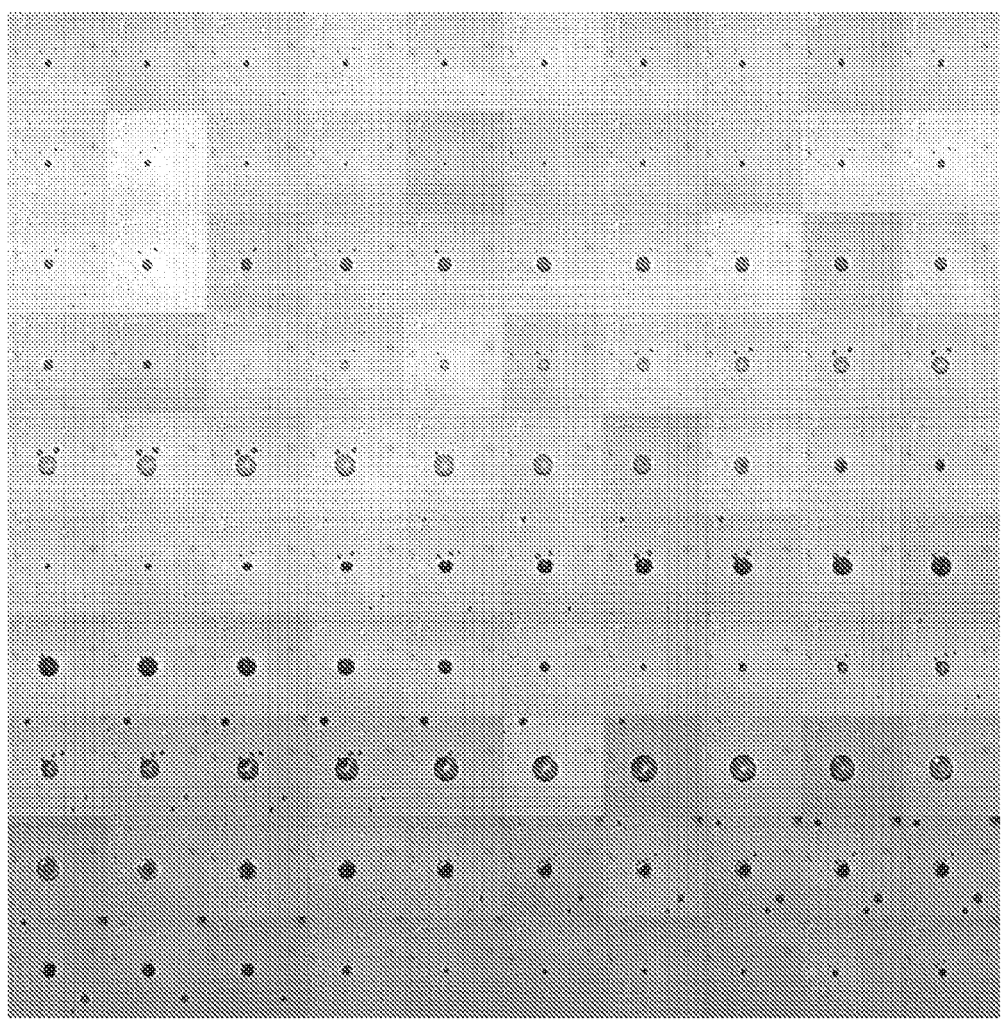
FIG. 8 illustrates an image of a lipid MB interacting with stem cells under ultrasound-selected frames of ultrasound induced MB vibration near a stem cell.

FIG. 8 illustrates an image of a lipid MB interacting with stem cells under ultrasound-selected frames of ultrasound induced MB vibration near a stem cell, demonstrating the potential therapeutic effect of ultrasound.

Figure 9:
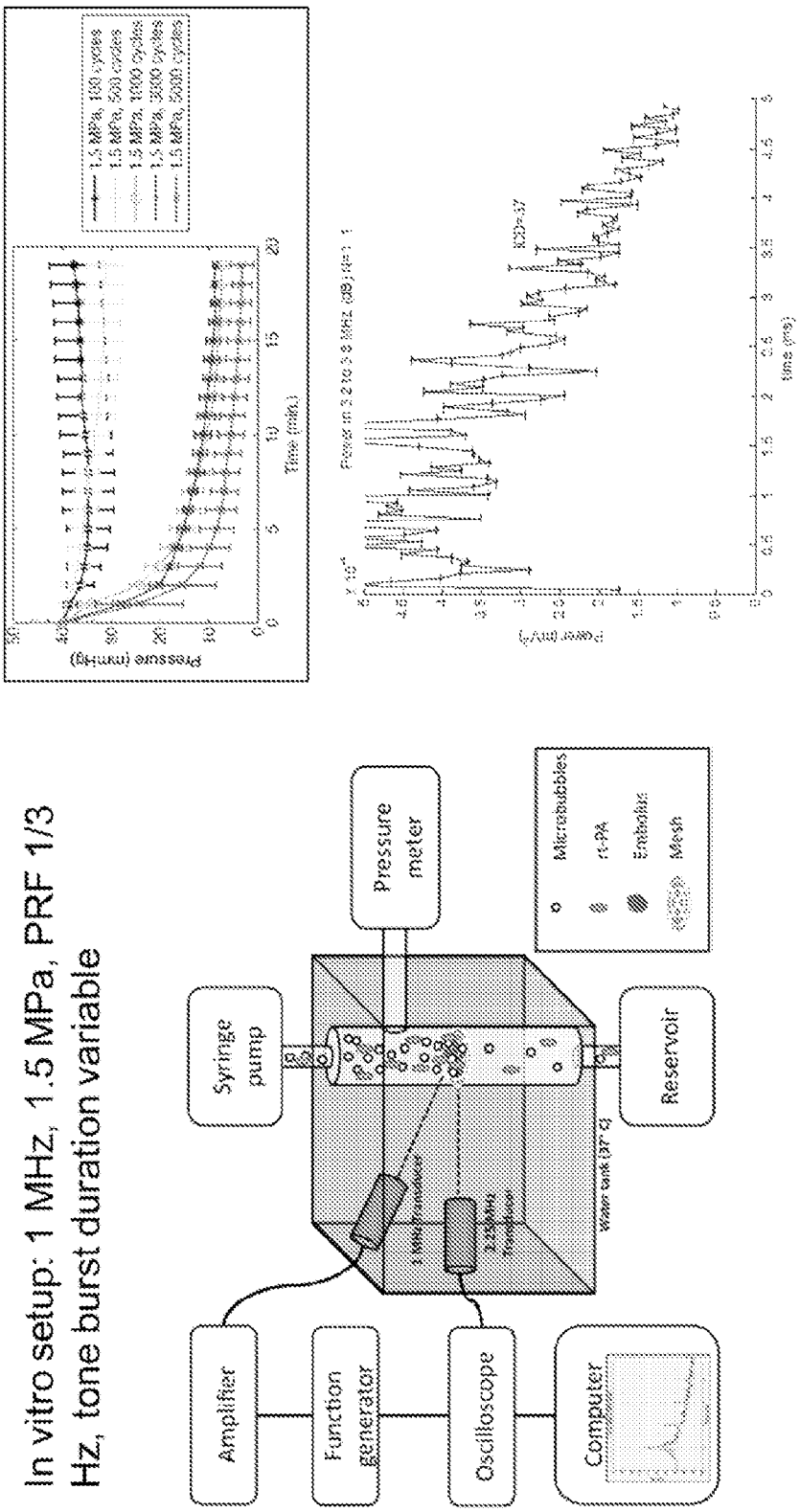
FIG. 9 illustrates an example application of long tone burst for sonothrombolysis in an in vitro setup.

FIG. 9 illustrates an example application of long tone burst for sonothrombolysis in a mock flow setup. In an in vitro model of sonothrombolysis, we found that there is a dependence of lytic effect on tone burst duration. Cavitation detection reveals continued but diminishing acoustic activity during 5 ms of ultrasound treatment.

Figure 10:
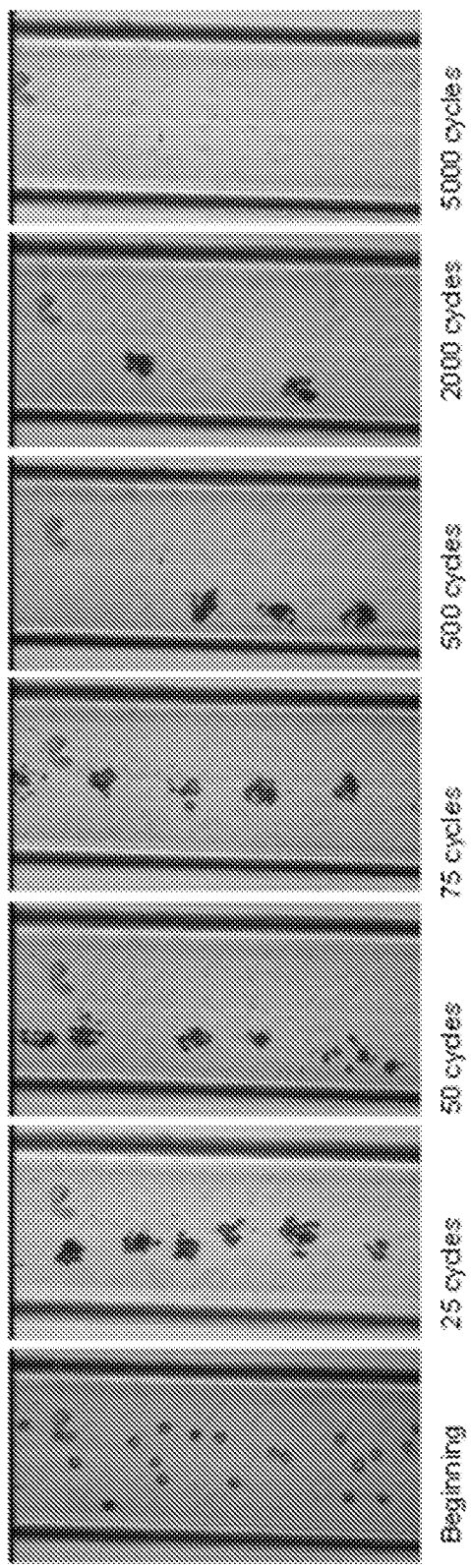
FIG. 10 illustrates an example application of long tone burst for therapeutic purposes with advanced time control of the high speed camera.

FIG. 10 shows long tone burst for therapeutic purposes with advanced time control of the high speed camera. The camera system can handle advanced trigger, up to 510 mirror cycles. For 5 Mfps (4000 rps, 250 µs), that means 125 ms. Even at 25 Mfps, the system can trigger accurately 25 ms ahead of time. Shown here are the behaviors of lipid MB at different time points of a 5000 cycle treatment. Notice that MB do not disappear. They form aggregates and continue to oscillate.

Figure 11:
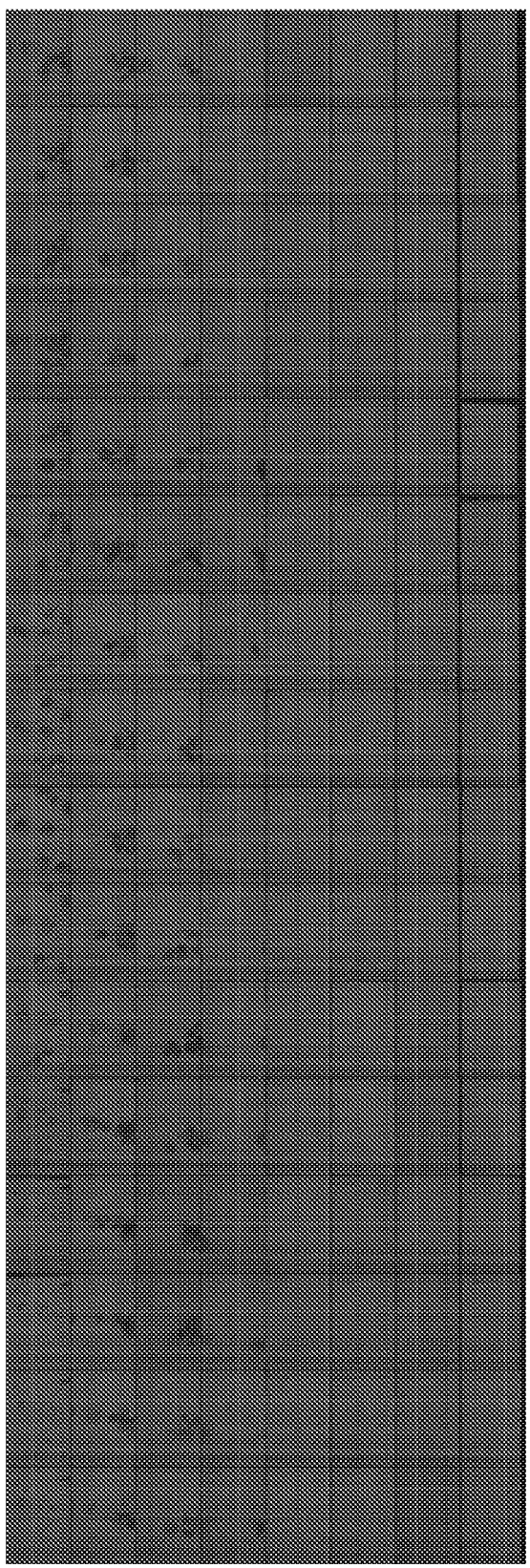
FIG. 11 illustrates frames of high speed movie showing the formation of aggregates at the early stage of a long tone burst.

FIG. 11 illustrates frames of high speed movie showing the formation of aggregates at the early stage of a long tone burst. For this example, the movie is taken at 0.5 Mfps, and the movie duration is 256 µs. Polymer MB. 1 MHz, 1.5 MPa. During this movie, aggregates of bubbles are formed. They continue to oscillate and the move out of view during imaging.

Figure 12:
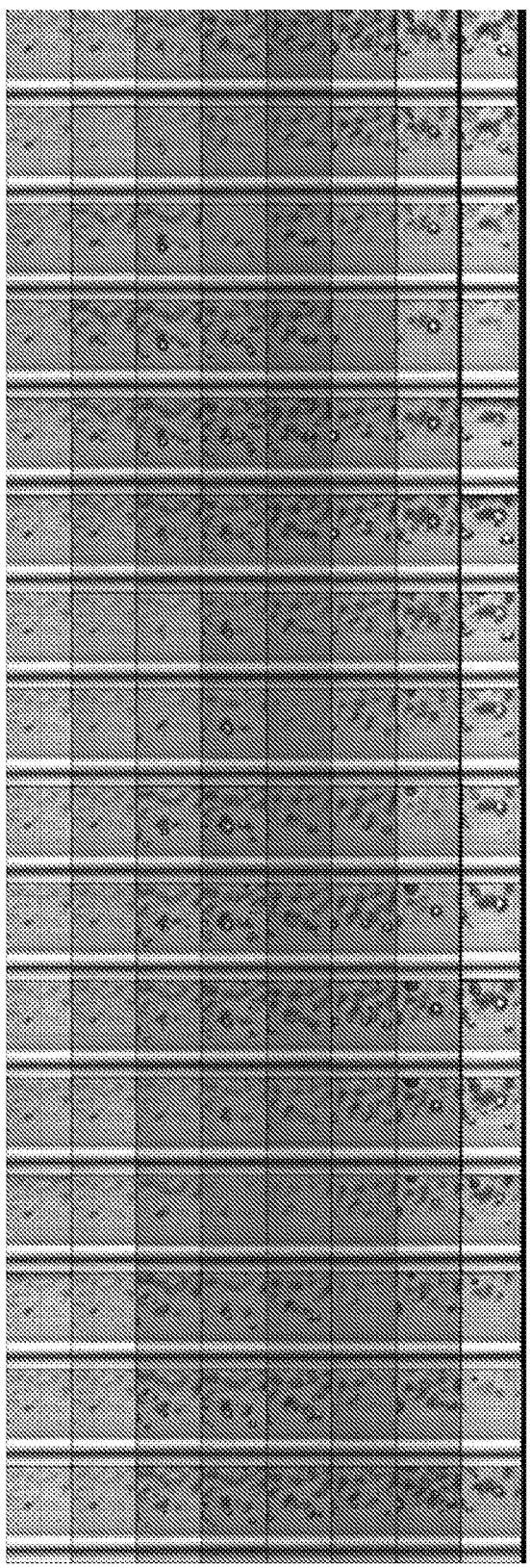
FIG. 12 illustrates frames of high speed movie showing the formation of aggregates at the beginning of a long tone burst.

FIG. 12 illustrates frames of high speed movie showing the formation of aggregates at the beginning of a long tone burst. For this example, the movie is taken at 5 Mfps, the movie duration is 25.6 µs. Polymer MB. 1 MHz, 1.5 MPa. During this movie, aggregates of bubbles are formed and continue to oscillate. The locations of the aggregates are random due to the dynamic nature of bubble destruction.

Figure 13:
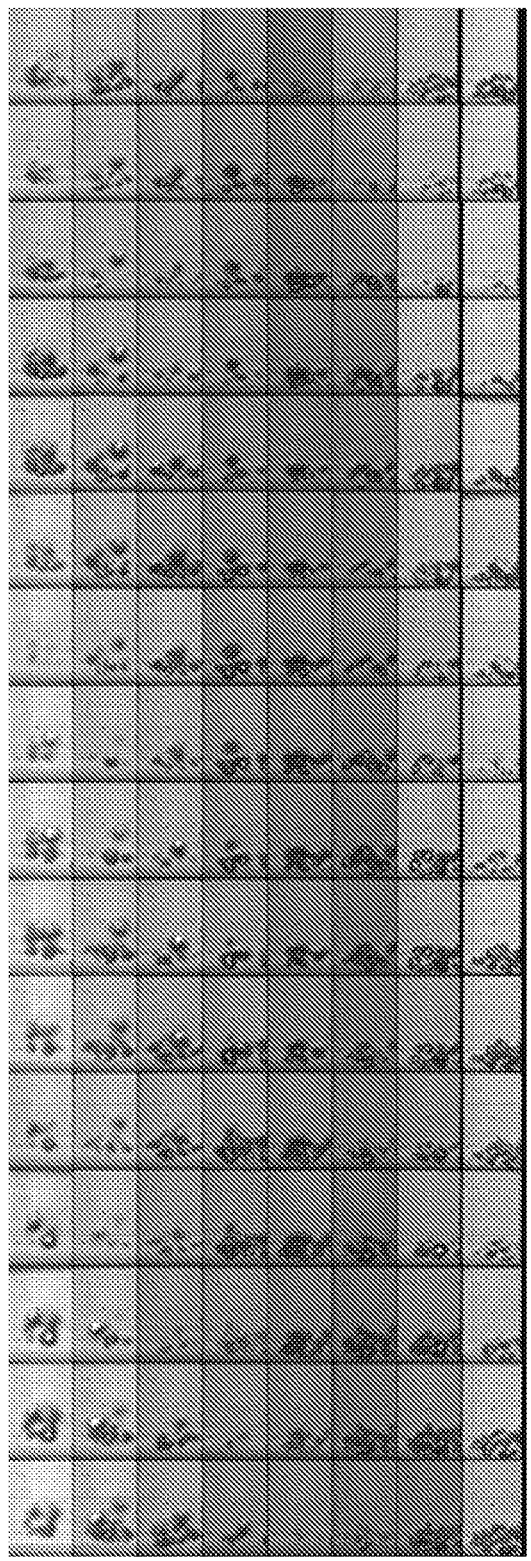
FIG. 13 illustrates frames of high speed movie showing the continued formation of aggregates at 500 acoustic cycles into a long tone burst.

FIG. 13 illustrates frames of high speed movie showing the continued formation of aggregates at 500 acoustic cycles into a long tone burst. For this example, the movie is taken at 5 Mfps, the movie duration is 25.6 µs. Polymer MB. 1 MHz, 1.5 MPa. During this movie, aggregates of bubbles continue to oscillate, break up and new aggregates are formed. The locations of the aggregates are random due to the dynamic nature of bubble destruction.

Figure 14:
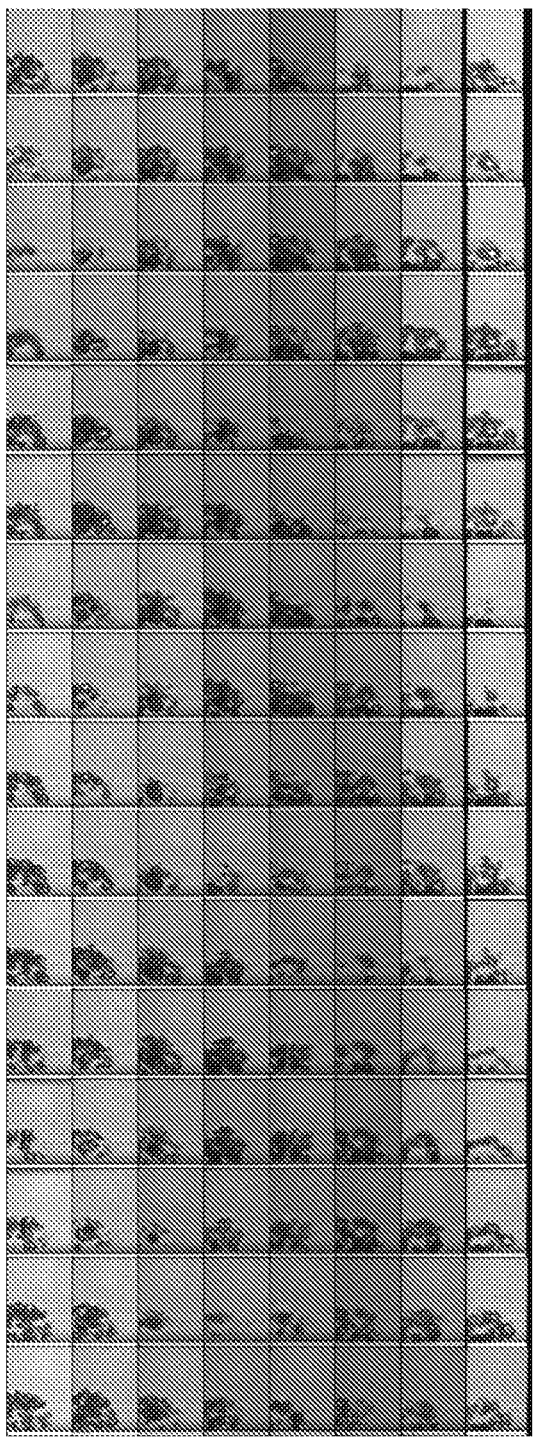
FIG. 14 illustrates frames of high speed movie showing the continued formation of aggregates 1,000 acoustic cycles into a long tone burst.

FIG. 14 illustrates frames of high speed movie showing the continued formation of aggregates 1,000 acoustic cycles into a long tone burst. For this example, the movie is taken at 5 Mfps, the movie duration is 25.6 µs. Polymer MB. 1 MHz, 1.5 MPa. During this movie, aggregates of bubbles continue to oscillate, break up and new aggregates are formed. The location of the aggregates is random due to the dynamic nature of bubble destruction.

Figure 15:
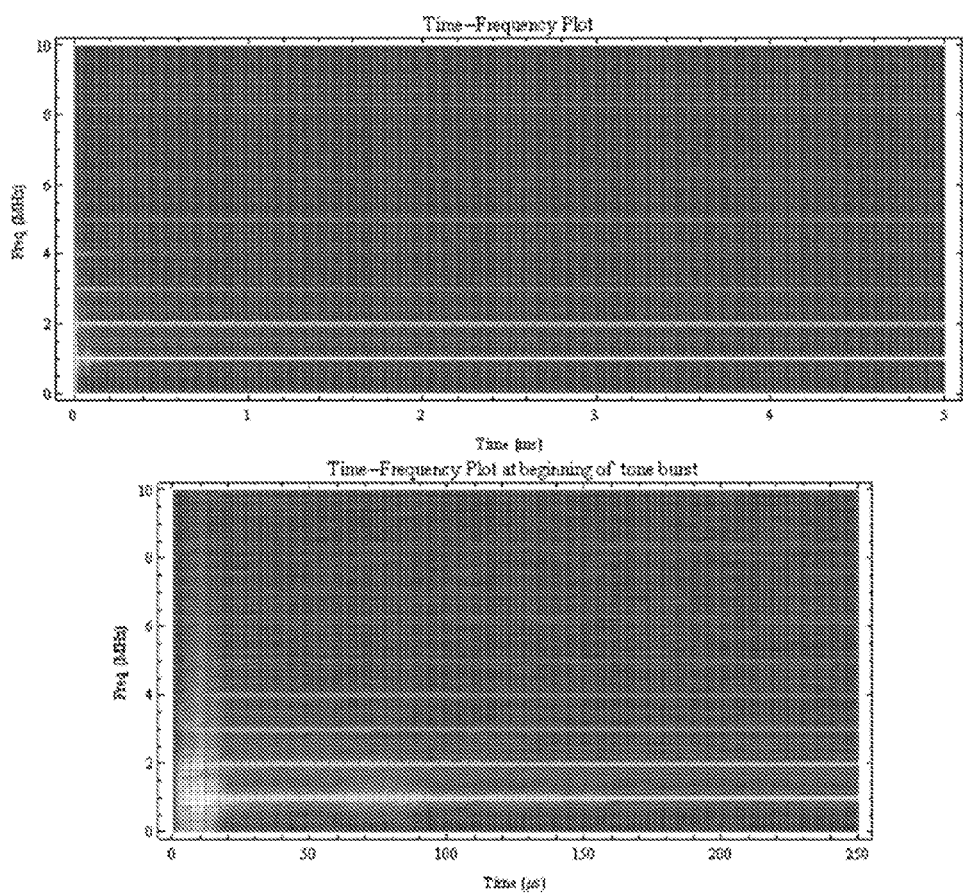
FIG. 15 illustrates a time-frequency analysis of lipid MB with PFC.

FIG. 15 illustrates a time-frequency analysis of lipid MB with PFC with a passive cavitation detection. Initial cavitation is detected at the beginning of tone bursts.

Figure 16:
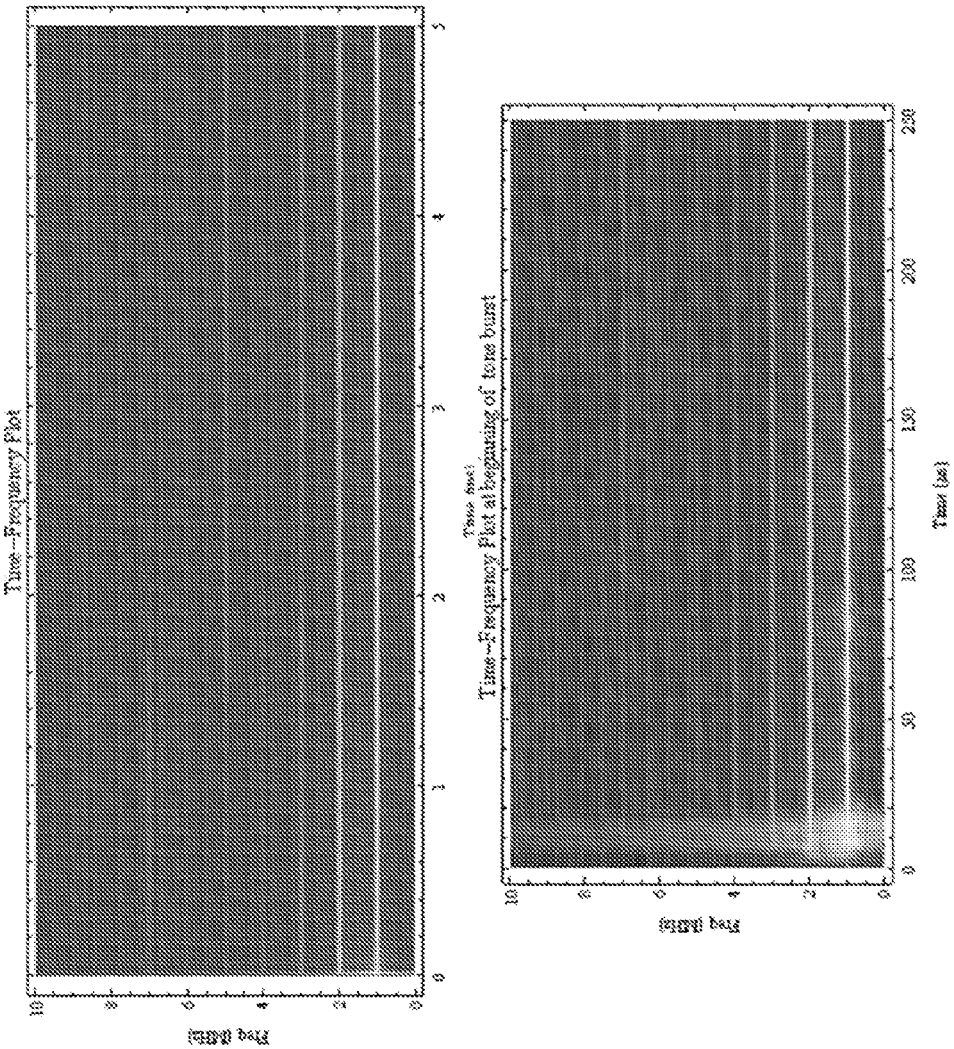
FIG. 16 illustrates a time-frequency analysis of polymer MB with PFC.

FIG. 16 illustrates a time-frequency analysis of polymer MB with PFC with a passive cavitation detection. Initial cavitation is detected at the beginning of tone bursts.

Figure 17:
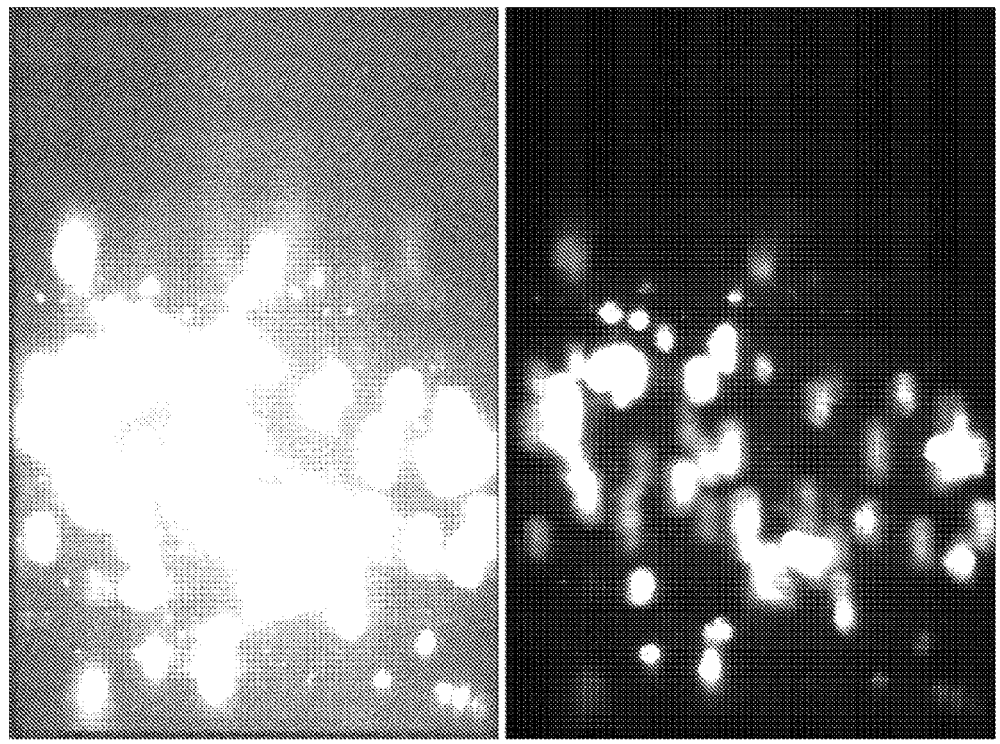
FIG. 17 illustrates images from a fluorescence movie illustrating that the beads are throwing off microbubble surface due to ultrasound induced oscillation and large movement (e.g., jetting).

FIG. 17 illustrates images from a movie illustrating that the beads are throwing off large movement (e.g., jetting). Lipid microbubble, 1 MHz, 1.5 MPa.

Figure 18:
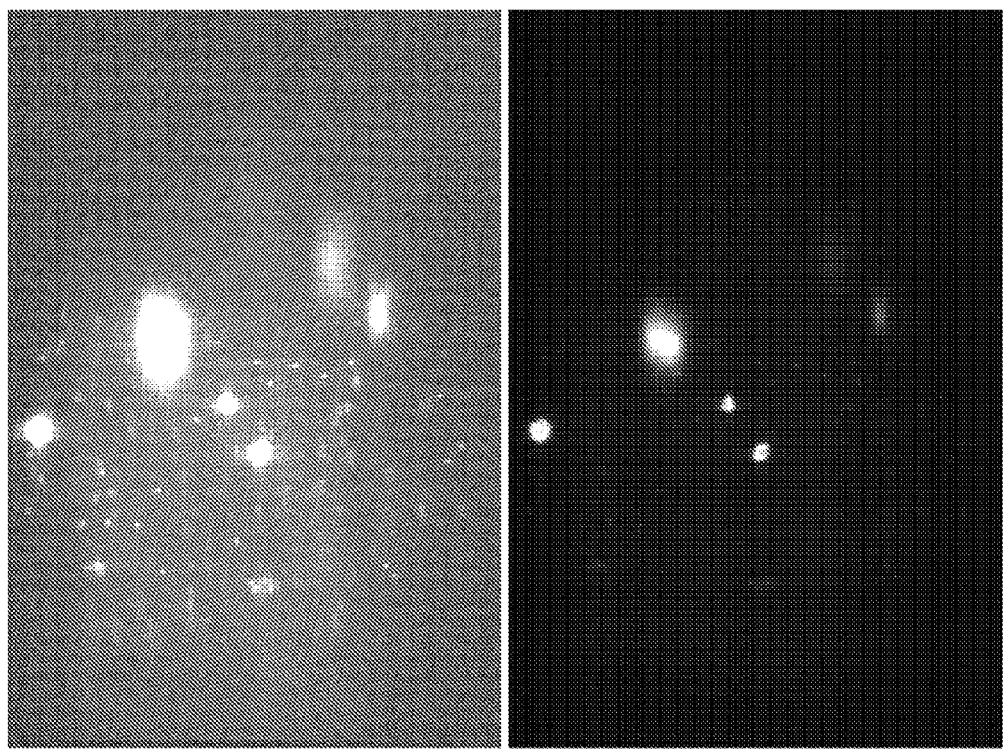
FIG. 18 illustrates additional images from a fluorescence movie illustrating that the beads are throwing off microbubble surface due to ultrasound induced oscillation.

FIG. 18 illustrates images from a movie illustrating that the beads are throwing off large movement (e.g., jetting). Lipid microbubble, 1 MHz, 1.0 MPa.

Figure 19:
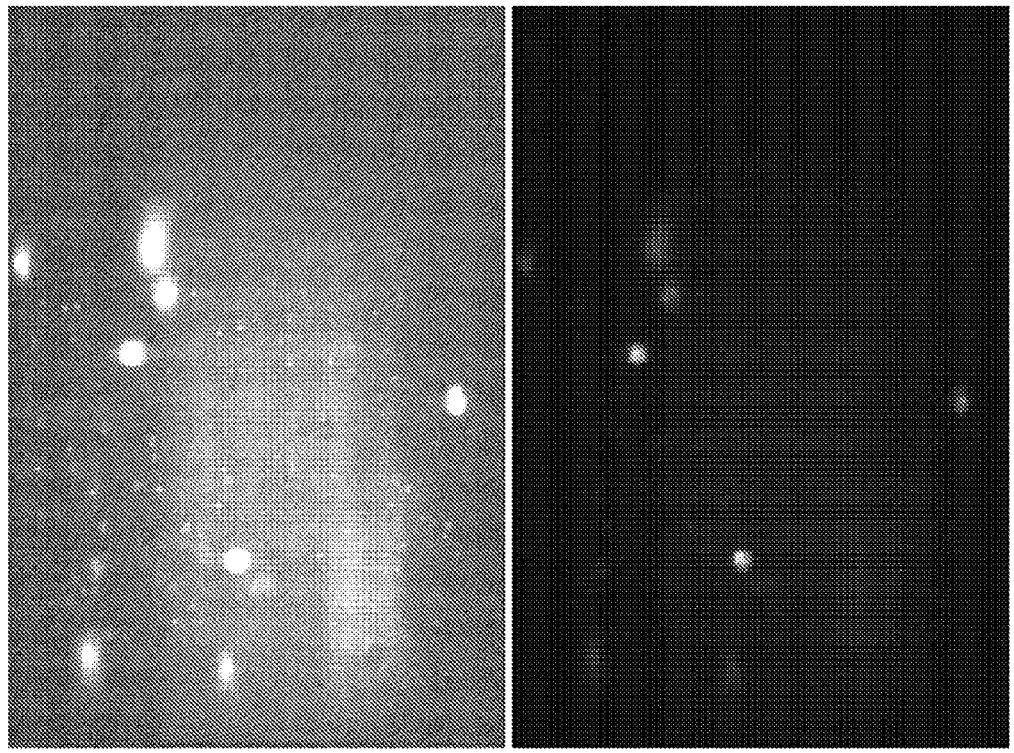
FIG. 19 illustrates additional images from a fluorescence movie illustrating that the beads are throwing off microbubble surface due to ultrasound induced oscillation.

FIG. 19 illustrates images from a movie illustrating that the beads are throwing off large movement (e.g., jetting). Lipid microbubble, 1 MHz, 0.5 MPa.

Figure 20:
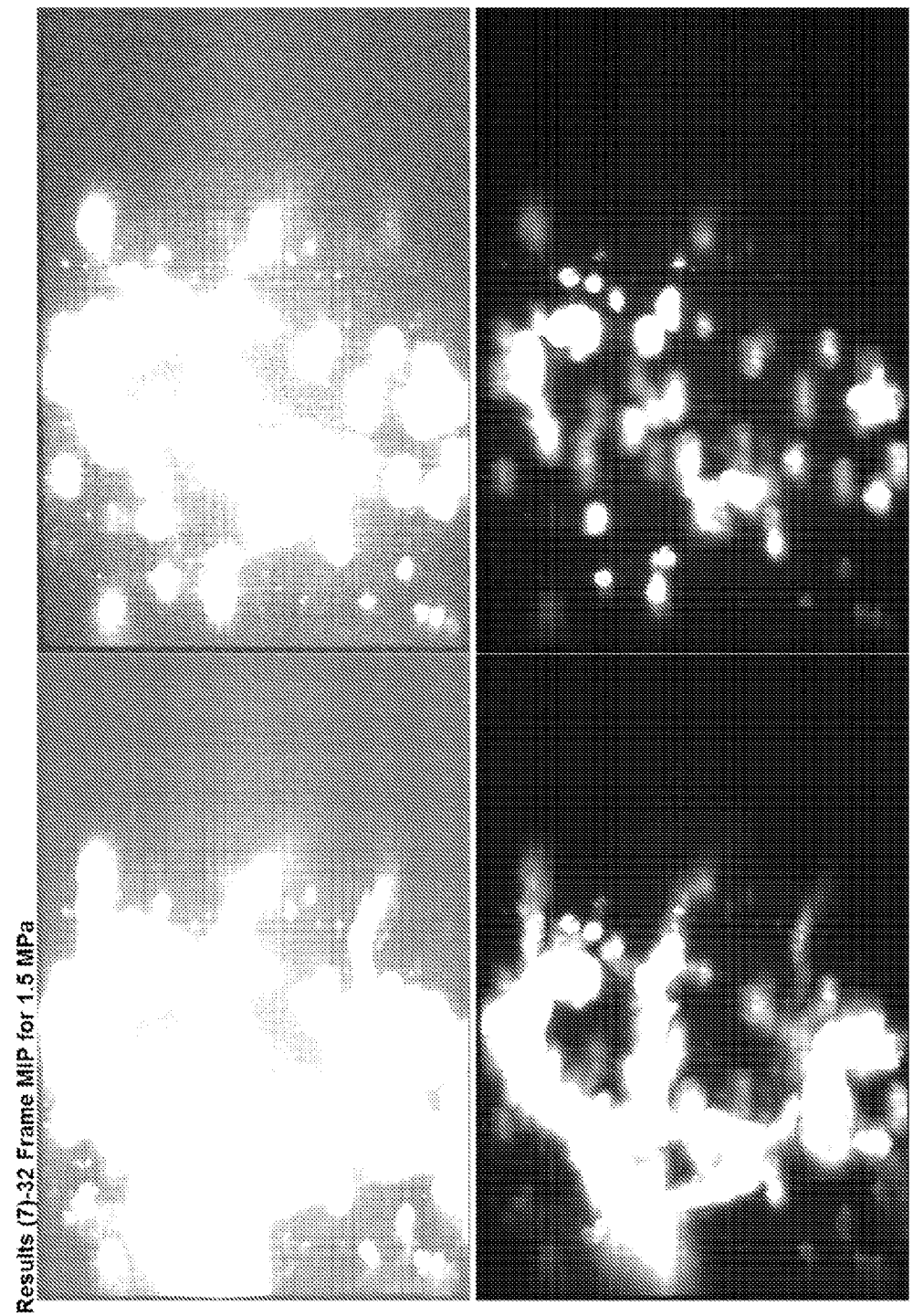
FIG. 20 illustrates a 32 frame MIP processing a fluorescence movie for 1.5 MPa.

FIG. 20 illustrates a 32 frame MIP processing a fluorescence movie. Lipid microbubble, 1 MHz, 1.5 MPa.

Figure 21:
FIG. 21 illustrates a 32 frame MIP processing a fluorescence movie for 1.0 MPa.

FIG. 21 illustrates a 32 frame MIP processing a fluorescence movie. Lipid microbubble, 1 MHz, 1.0 MPa.

Figure 22:
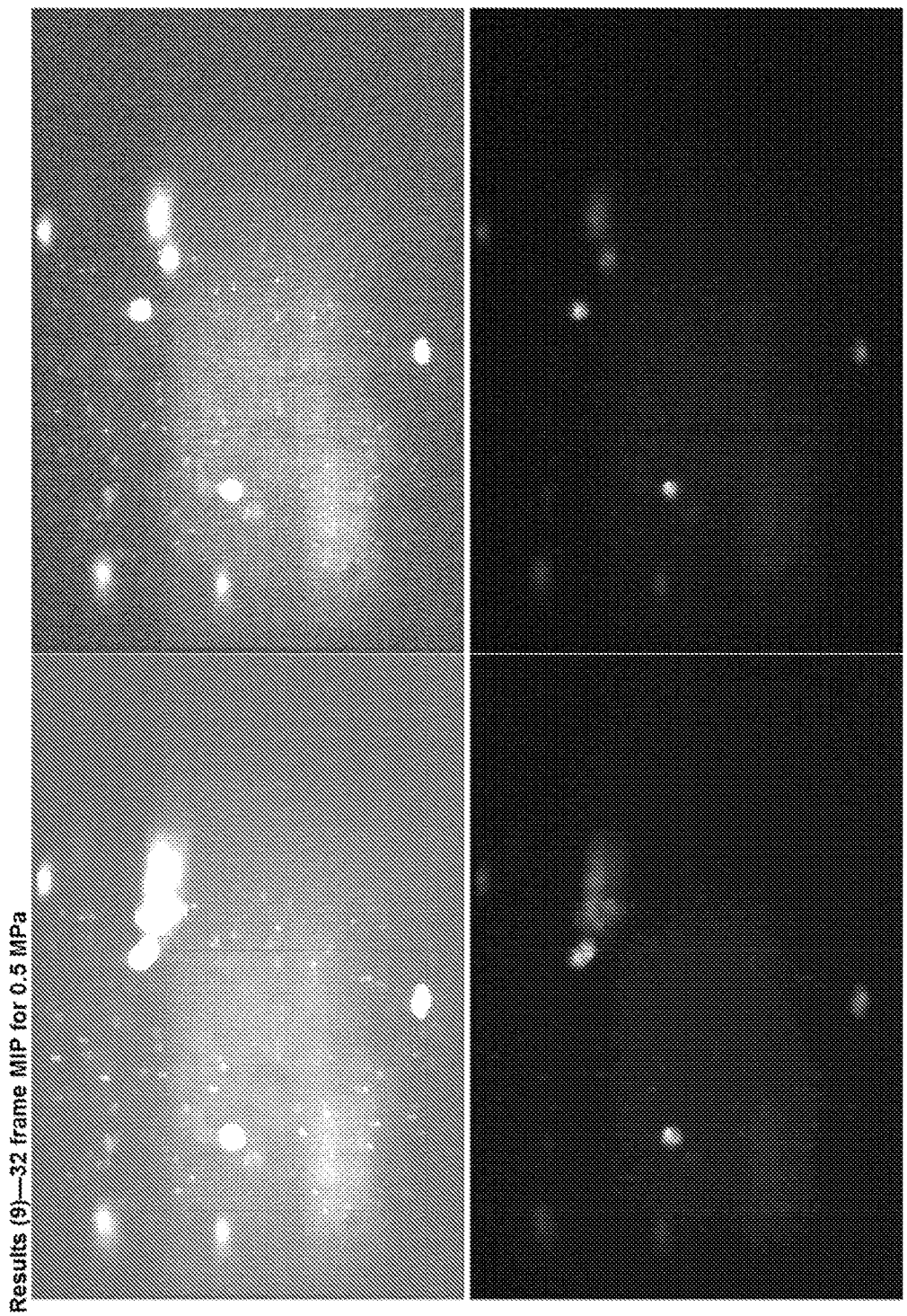
FIG. 22 illustrates a 32 frame MIP processing a fluorescence movie for 0.5 MPa.

FIG. 22 illustrates a 32 frame MIP processing a fluorescence movie. Lipid microbubble, 1 MHz, 0.5 MPa.

Figure 23:
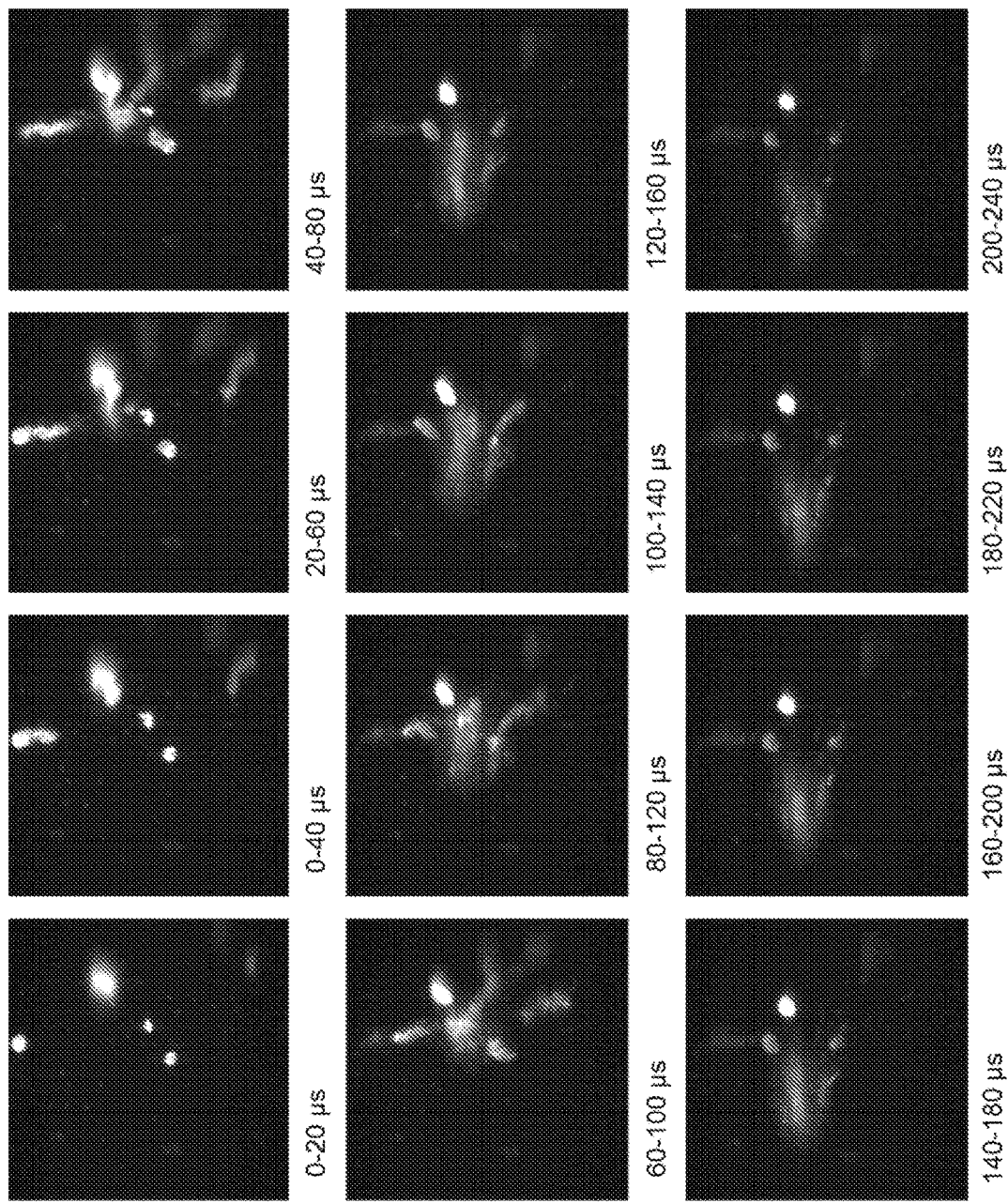
FIG. 23 illustrates microjet formation during ultrasound excitation of MB recorded with high speed fluorescence imaging at 0.5 Mfps.

FIG. 23 illustrates microjet formation during ultrasound excitation of MB recorded with high speed fluorescence imaging at 0.5 Mfps. Displayed are selected frames from a rolling maximum intensity persistence processing of the high speed movie. Ultrasound parameters: 1 MHz, 1 MPa. Image size: 92×92 µm.

Figure 24:
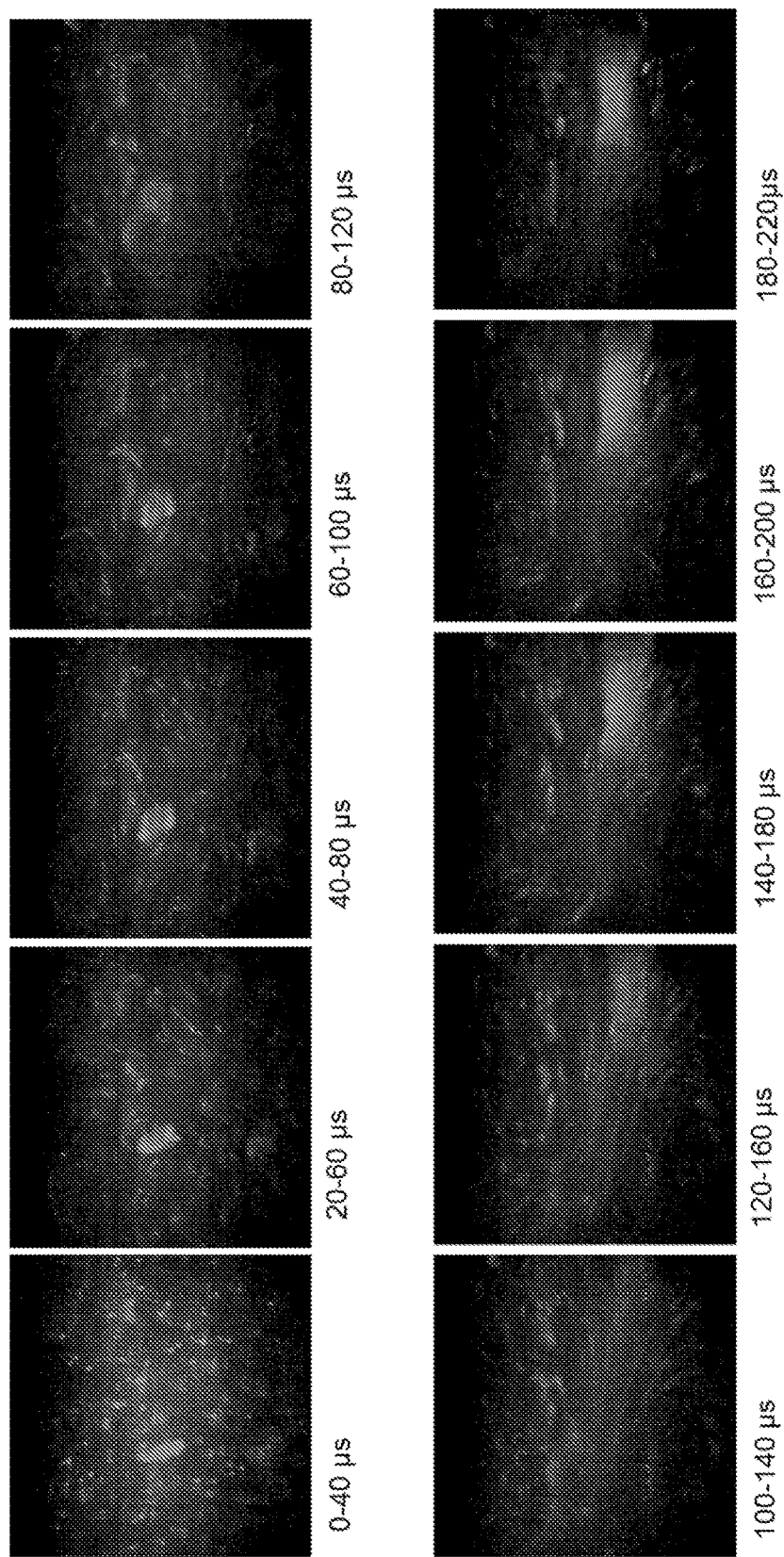
FIG. 24 illustrates microjet formation during ultrasound excitation of MB recorded with high speed fluorescence imaging at 0.5 Mfps.

FIG. 24 illustrates microjet formation during ultrasound excitation of MB recorded with high speed fluorescence imaging at 0.5 Mfps. Displayed are selected frames from maximum intensity persistence processing (with 50% overlap) of the high speed movie. Ultrasound parameters: 1 MHz, 1.5 MPa. Image size: 92×92 µm.

Accordingly, a high speed imaging system for visualization of microbubble acoustic behaviors is used for the study of ultrasound microbubble mediated therapy. Accordingly, as illustrated herein such as in FIG. 10-14, MBs can persist after the initial burst; even though broadband noise due to initial cavitation is detected only in the beginning of the tone burst and decreased as a function of time with a simple detection strategy. Accordingly, the efficacy of long tone burst for sono-thrombolysis and other ultrasound assisted therapy is validated by the presence to bubble activity observed with high speed imaging.

Long Tone Burst on Ultrasound Assisted Thrombolysis

In some embodiments, the method comprises the use of relatively long acoustic ultrasound (US) tone bursts in conjunction with microbubble-based (MB) ultrasound contrast agents. The MB ultrasound contrast agent can be used with or without thrombolytic agents, such as tissue plasminogen activator (tPA) for thrombolysis. The MB ultrasound contrast agent can also be used with or without drug and/or gene loaded microbubbles for treatment of cancer or other medical conditions requiring drug or molecular therapeutics.

In the embodiments disclosed herein, the specific attributes of the pulse waveform can vary based on the frequency desired for certain tissue types and organ size, the type of microbubble used, and the US pressure amplitude. For example, typically, a tone burst of greater than 5 acoustic cycles is used. For example, typically, a tone burst ranging from 10-5,000 acoustic cycles is used (with a range of 1,000-2,000 acoustic cycles being preferred for some embodiments) with a pulse repetition frequency (PRF) that allows replenishment of the MB into the region of interest (ROI). In some embodiments, a PRF range of 0.01-20 Hz can be used, with a range of 0.2-1 Hz being preferred in certain embodiments. An ultrasound frequency of 0.25 MHz-10 MHz can be used in some embodiments, with a frequency range of 1-2 MHz being preferred for certain embodiments, as those frequencies are close to the resonance frequency of some of the microbubbles present in contrast agents described herein. In addition, pressure amplitude of greater than 0.3 MPa can be used. In addition, a pressure amplitude of 0.5-1.9 MPa (and, more preferably 1.5 MPa in some embodiments) can be used.

The embodiments disclosed herein demonstrate that microbubbles can persist longer than previously reported when subjected to US excitation above cavitation threshold with ultra-fast microscopic imaging. Using the methods and systems described herein the MB go through initial cavitation, form aggregates, and continue to oscillate during US delivery of up to 5,000 acoustic cycles, depending on the acoustic pressure and type of MB used. Such prolonged acoustic activity can promote continued micro-streaming and mass transport for therapeutic materials such as tPA and cancer therapy drugs. In addition, the prolonged acoustic activity can, at least in some embodiments, also promote continued sonoporation of cells and possible mass transport for materials like cancer drugs or gene vectors once they enter the cancer cells through sonoporation.

In some embodiments, the methods and systems described herein can provide improved cancer therapy by reducing systemic exposure to cancer therapy agents. In addition, the relatively low PRF reduces the total amount of US energy and therefore reduces at least some potential bioeffects, such as heating. For example, when a 2,000 acoustic cycle tone burst of 1.5 MPa acoustic pressure is used at a PRF of 0.5 Hz, the duty cycle is 0.1%, and the time averaged ultrasound intensity is only 0.075 W/cm$^2$.

In some embodiments, a device is provided that includes an ultrasound generator and ultrasound transducer that can produce US waveforms. The ultrasound generator can be configured such that the ultrasound pulse configuration can be changed online according to specific microbubble properties and blood flow conditions. This can permit the total ultrasound energy to be minimized while still harnessing most of the bubble activity for therapeutic purposes. The ultrasound generator can be a self-contained unit or an attachment or an add-on of another system such as an ultrasound imaging system. The ultrasound transducer can be a single element transducer with or without focusing. For example, the transducer can be a spherically-focused or cylindrically-focused transducer depending on the type of tissue/or organ to be treated. The transducer can also be formed by an array of elements to allow dynamic focusing of the ROI.

In some embodiments, the transducer can also be constructed to allow imaging of microbubble activity. For this mode of application, the transducer can be broadband or capable of dual frequency applications such that better image resolution is achieved with high frequency. The ultrasound transducer can also be designed such that imaging can be performed with third party imaging systems.

ACOUSTIC BEHAVIOR EXAMPLES

As described above, the use of MB and long tone bursts can be effective for sonothrombolysis and other ultrasound assisted therapies. Both Lipid MB and Polymer MB are effective to improve sonothrombolysis at least in part because MB's persist after the initial burst and continue to oscillate with large amplitudes during a long tone burst, before ultimately diminishing.

As discussed above and depicted in the figures, optimal tone burst length can depend on the acoustic pressure, the bubble type, and the bubble concentration. Accordingly, the methods disclosed herein can include a step of selecting an optimal tone burst length based on acoustic pressure, bubble type, bubble concentration, and/or any combination of the three. As shown in the figures, in some embodiments, longer cycle lengths (e.g., 5000 cycles) can provide an improved response when compared to shorter cycle length (e.g., 1000 cycles). As discussed below, larger cycle lengths can be particularly beneficial when bubble concentrations are higher and where initial cavitation can last longer (e.g., 5000 cycles).

Figure 25:
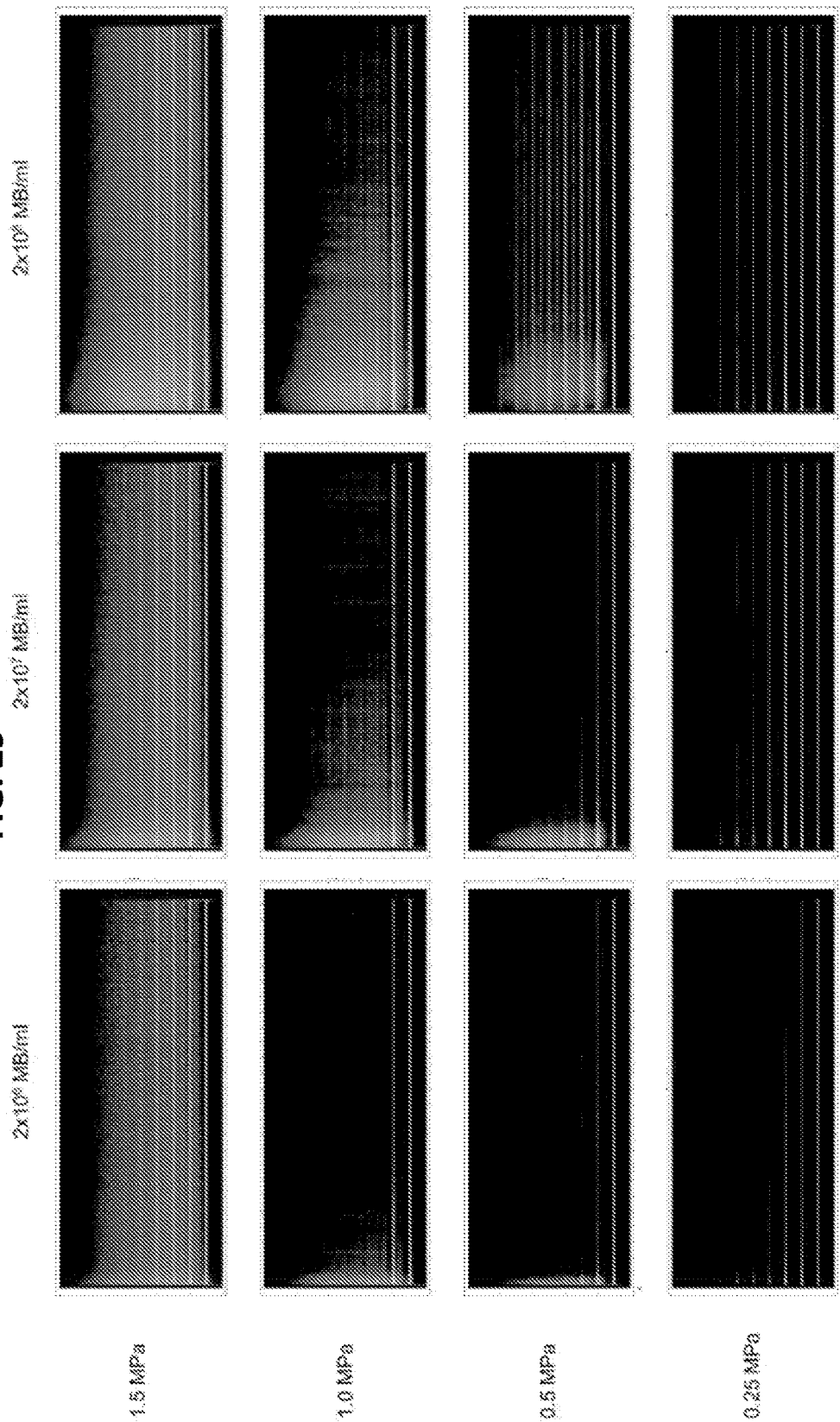
FIG. 25 shows several time-frequency analysis that compare polymer MB (i.e., polymer MB with PFC) response at different MB concentrations and different acoustic pressures.

FIG. 25 show time-frequency analysis that compare polymer MB (i.e., polymer MB with PFC) response at different MB concentrations and different acoustic pressures over a time period of 5000 cycles. For example, the far left column shows acoustic responses of polymer MB at a first concentration ($2\times10^6$ MB/ml) taken at different acoustic pressures (1.5 MPa, 1.0 MPa, 0.5 MPa, and 0.25 MPa), the middle column shows acoustic responses of polymer MB at a second concentration ($2\times10^7$ MB/ml) taken at different acoustic pressures (1.5 MPa, 1.0 MPa, 0.5 MPa, and 0.25 MPa), and the far right column shows acoustic responses of polymer MB at a third concentration ($2\times10^8$ MB/ml) taken at different acoustic pressures (1.5 MPa, 1.0 MPa, 0.5 MPa, and 0.25 MPa).

Figure 26:
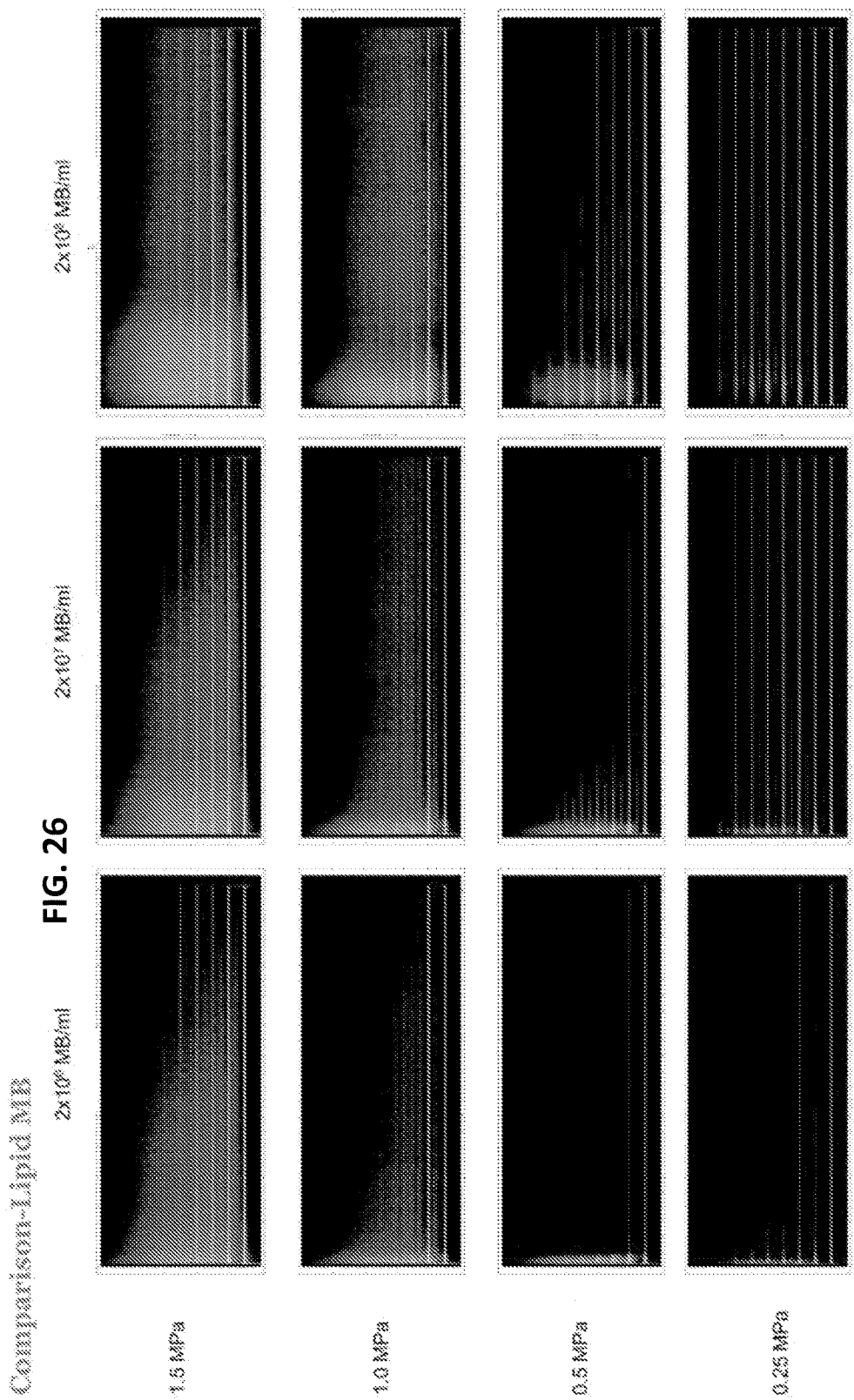
FIG. 26 shows several time-frequency analysis that compare polymer MB (i.e., polymer MB with PFC) response at different MB concentrations and different acoustic pressures.

FIG. 26 is similar to FIG. 25, but shows a comparison of lipid MB (i.e., lipid MB with PFC) at different MB concentrations and different acoustic pressures. For example, the far left column shows acoustic responses of lipid MB at a first concentration ($2\times10^6$ MB/ml) taken at different acoustic pressures (1.5 MPa, 1.0 MPa, 0.5 MPa, and 0.25 MPa), the middle column shows acoustic responses of lipid MB at a second concentration ($2\times10^7$ MB/ml) taken at different acoustic pressures (1.5 MPa, 1.0 MPa, 0.5 MPa, and 0.25 MPa), and the far right column shows brightfield responses of lipid MB at a third concentration ($2\times10^8$ MB/ml) taken at different acoustic pressures (1.5 MPa, 1.0 MPa, 0.5 MPa, and 0.25 MPa).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating a thrombotic condition by performing ultrasound contrast assisted therapy comprising:
   delivering a plurality of microbubble-based ultrasound contrast agents to a target area of a subject, the target area comprising a thrombus which is in a vessel or microvessels; and
   disrupting the plurality of microbubble-based ultrasound contrast agents by delivering a pulse sequence of ultrasound tone bursts to the target area from a location external to the vessel or microvessels, and causing oscillations of the microbubble-based ultrasound contrast agents against the thrombus, the pulse sequence consisting of:

ultrasound tone bursts that are each of greater than 500 acoustic cycles with a pulse repetition frequency of between 0.01 and 20 Hz and a pressure amplitude that is greater than 0.5 MPa for the duration of each of the ultrasound tone bursts, and an ultrasound frequency is between 0.25 MHz and 10 MHz, wherein the pulse sequence has a time averaged ultrasound intensity that is less than 0.5 W/cm$^2$.

2. The method of claim 1, wherein at least some of the plurality of microbubble-based ultrasound contrast agents comprise a treatment agent.

3. The method of claim 2, wherein the treatment agent comprises a drug.

4. The method of claim 2, wherein the treatment agent comprises one or more genes.

5. The method of claim 2, wherein the treatment agent comprises one or more anti-thrombus agents.

6. The method of claim 2, wherein the treatment agent comprises a protein.

7. The method of claim 6, wherein the treatment agent comprises a thrombolytic agent.

8. The method of claim 7, wherein the thrombolytic agent is tissue plasminogen activator.

9. The method of claim 1, wherein the ultrasound tone bursts are greater than 500 acoustic cycles and less than 50,000 acoustic cycles.

10. The method of claim 1, wherein the ultrasound tone bursts are greater than 500 acoustic cycles and less than 2,000 acoustic cycles.

11. The method of claim 1, wherein the pulse repetition frequency is between 0.2 and 1 Hz.

12. The method of claim 1, wherein the pressure amplitude of ultrasound pulses forming the ultrasound tone bursts is greater than 0.5 MPa and less than 1.9 MPa.

13. A method of performing sonothrombolysis comprising:

delivering a plurality of microbubble-based ultrasound contrast agents to a target area of a subject comprising a thrombus which is in a vessel or microvessels; and delivering a pulse sequence of long tone bursts of ultrasound to the target area from a location external to the vessel or microvessels to cause the plurality of microbubble-based ultrasound contrast agents to cavitate, the pulse sequence consisting of:

long tone bursts having a length of at least 500 acoustic cycles, an ultrasound frequency between 0.25 MHz and 10 MHz, a pulse repetition frequency of between 0.01 and 20 Hz, and a pressure amplitude that is not less than 1.0 MPa for the duration of the long tone bursts wherein the plurality of microbubble-based ultrasound contrast agents are selected so that after cavitation, aggregates of the bubbles continue to oscillate, break up, and form new aggregates during the delivery of the plurality of long tone bursts.

14. The method of claim 13, wherein the plurality of long tone bursts have a length of 1000 acoustic cycles or greater.

15. The method of claim 13, wherein the plurality of long tone bursts have a length of between 1000 acoustic cycles and 5000 acoustic cycles.

16. The method of claim 13, wherein the plurality of long tone bursts are delivered with a pulse repetition frequency that is between 0.2 and 1 Hz.

* * * * *